United States Patent
Bengs et al.

(10) Patent No.: US 7,097,831 B1
(45) Date of Patent: *Aug. 29, 2006

(54) α-AMYLASE-RESISTANT STARCH FOR PRODUCING FOODSTUFF AND MEDICAMENTS

(75) Inventors: Holger Bengs, Frankfurt (DE); Anette Brunner, Roth (DE)

(73) Assignee: Südzucker Aktiengesellschaft Mannheim/Ochsenfurt, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/869,398

(22) PCT Filed: Nov. 30, 1999

(86) PCT No.: PCT/EP99/09298

§ 371 (c)(1),
(2), (4) Date: Nov. 13, 2001

(87) PCT Pub. No.: WO00/38537

PCT Pub. Date: Jul. 6, 2000

(30) Foreign Application Priority Data

Dec. 28, 1998 (DE) ................................ 198 60 375

(51) Int. Cl.
*A01N 63/00* (2006.01)

(52) U.S. Cl. ..................... 424/93.4; 424/93.45; 514/60; 514/778; 536/102; 435/101; 426/658; 426/661

(58) Field of Classification Search ............... 424/93.4, 424/93.45; 514/60, 778; 536/102; 435/101; 426/658, 661
See application file for complete search history.

(56) References Cited

U.S. PATENT DOCUMENTS

| | | | | |
|---|---|---|---|---|
| 5,409,542 A | * | 4/1995 | Henley et al. | 127/65 |
| 5,480,669 A | * | 1/1996 | Zallie et al. | 426/549 |
| 6,696,563 B1 | * | 2/2004 | Bengs et al. | 536/123.12 |

FOREIGN PATENT DOCUMENTS

| | | | |
|---|---|---|---|
| DE | 19830618 | | 1/2000 |
| EP | 506166 | | 9/1992 |
| EP | 688872 | | 12/1995 |
| EP | 727485 | | 8/1996 |
| EP | 846704 | | 6/1998 |
| JP | 07313069 | | 12/1995 |
| WO | WO 9204832 | | 4/1992 |
| WO | WO 95/31553 | * | 11/1995 |
| WO | WO 96/08261 | * | 3/1996 |
| WO | WO 9734932 | | 9/1997 |

OTHER PUBLICATIONS

International Search Report of Mar. 29, 2000.
German Search Report Oct. 7, 1999.

* cited by examiner

*Primary Examiner*—Francisco C. Prats
(74) *Attorney, Agent, or Firm*—Gilberto M. Villacorta; Matthew E. Mulkeen; Foley & Lardner LLP

(57) ABSTRACT

The invention relates to foodstuff and animal feed which contain resistant starch on the basis of water-insoluble linear α-1,4-D-glucans. The invention also related to the utilization of resistant starch on the basis of water-insoluble linear α-1,4-D-glucans as medicaments.

21 Claims, No Drawings

α-AMYLASE-RESISTANT STARCH FOR PRODUCING FOODSTUFF AND MEDICAMENTS

The invention relates to compositions which comprise α-1,4-D-glucans and/or a resistant starch therefrom for producing foodstuffs. The invention further relates to the use of resistant starch as medicaments.

Nutritional studies have found that malnutrition and unbalanced nutrition are the reason for numerous disorders, for example gastric disorders and in particular carcinomas of the colon. Epidemiological studies have found that in a high-fat and low-fiber diet, there is an increased risk of the formation of inflammatory gastric disorders and colon cancer in humans. In contrast, a protective effect to colorectal disorders is ascribed to a high-fiber diet.

The production of what is termed functional food, i.e. foods which not only act in nutrition but are also intended to promote health, has therefore increased in importance recently. Such foods are enriched with additives having a health-promoting action.

One of the additives which has achieved increasing importance for the food industry is resistant starch (RS), i.e. starch which is not degraded by α-amylases. Resistant starch is therefore not digested in the small intestine of healthy humans, and thus passes into the large intestine. Resistant starches in foods are thus a reduced-energy component, providing body in the sense of a dietary fiber.

However, the intake of RS-containing foods is also linked to two other functions, viz. providing substrates for the energy metabolism of the intestinal microflora and that of the large intestine epithelial cells. Resistant starch is degraded by the intestinal microorganisms by oxidation to form short-chain fatty acids, such as acetate, propionate and butyrate. These short-chain fatty acids in turn are used by the large intestine epithelial cells which are particularly dependent on luminal supply of butyrate, for maintenance of their structure and function.

A high luminal butyrate level in the colon can, in addition, be a protective factor against colorectal disorders. This is because while butyrate, in normal colonocytes, controls growth via a chain of reactions which, in normal colon epithelial cells increases proliferation, it apparently suppresses the neoplastic development of colonocytes.

Resistant starches occur naturally only in a small amount and are formed during recrystallization (retrogradation) of gelatinized starch. Microcrystalline filaments form which develop a network, which prevents enzymatic hydrolysis.

Resistant starches, processes for their production and their use in foods have long been known.

Thus U.S. Pat. No. 3,729,380 describes the targeted enzymatic treatment of starch to reduce the content of highly branched amylopectin and to increase the proportion of short-chain amylose structures, which usually have a greater tendency to retrogradation and thus to the formation of resistant starch, than native starches.

EP-A-0 564 893 describes a process for producing RS products in which an aqueous suspension of a starch is gelatinized and is debranched with an enzyme which cleaves the α-1,6-glycosidic bonds. The resultant intermediate is then retrograded.

EP-A-0 688 872 describes a process for producing RS products in which an aqueous suspension of a partially degraded, gelatinized starch is enzymatically debranched and the intermediate retrograded.

U.S. Pat. No. 5,776,887 discloses a food composition for diabetics having various carbohydrate fractions which are absorbed at different speeds. The slowly absorbed fraction consists of a corn starch which also has a content of resistant starch. U.S. Pat. No. 5,776,887 has as its object releasing carbohydrates uniformly over a relatively long period in order to avoid excess glucose levels.

However, there continues to be a great need for improved foodstuffs and preparations which, by supplying health-promoting substances, increase the well-being of the consumer, can prevent malnutrition and can assist in during disorders, for example those of a nutritional nature.

It is an object of the present invention, therefore, to provide, firstly, foods and feeds (below termed collectively foodstuffs) and, secondly, pharmaceutical and veterinary compositions (termed collectively medicaments below) which promote maintenance of health, increase well-being and can be used for treating and/or preventing disorders, in particular due to malnutrition in humans or animals.

This object was achieved by using water-insoluble linear α-1,4-D-glucans in combination with food or feed additives for producing the abovementioned products. In this context, the present invention is to be understood as a further development of the earlier DE-A-198 30 618, which was not published before the present application, and describes the use of water-insoluble α-1,4-D-glucans for producing resistant starch.

The present invention therefore relates to compositions, in particular for dietary supplementation, which comprise a water-insoluble linear α-1,4-D-glucan and/or a resistant starch obtainable therefrom and at least one further food additive or feed additive.

The invention further relates to foodstuffs which are obtainable using these compositions.

The present invention further relates to the use of resistant starch based on water-insoluble linear α-1,4-D-glucans as a substitute and/or calorie-reducing agent in foodstuffs.

The present invention finally relates to the use of resistant starches based on water-insoluble linear α-1,4-D-glucans as medicaments and pharmaceutical or veterinary compositions which comprise such resistant starches.

Surprisingly it has been found that water-insoluble linear α-1,4-D-glucans during retrogradation deliver in great quantity highly resistant starch, in particular type RS-III (Englyst et al. (Classification and measurement of nutritionally important starch Fractions, European Journal of Clinical Nutrition, 46 (Suppl. 23) (1992) 33–50).

This makes these resistant starches suitable as a substitute for foodstuff constituents, in particular as a substitute for dietary fiber and as a fat substitute and thus also as a calorie-reducing agent.

It has further been found that the resistant starch obtainable from water-insoluble linear α-1,4-D-glucans, during degradation in the large intestine, leads not only to a large amount of short-chain fatty acids, but in particular also to a high proportion of the particularly advantageous butyrates.

It has further been found that the resistant starch obtainable from water-insoluble linear α-1,4-D-glucans, in combination with other food additives or feed additives, exhibits a synergistic or symbiotic effect, the effects of the components intensifying one another.

Water-insoluble linear α-1,4-D-glucans are taken to mean below the non-α-amylase-resistant forms of these glucans.

Water-insoluble α-1,4-D-glucans are taken to mean in this case α-1,4-D-glucans which, in accordance with the definition of the German Pharmacopeia (DAB, Wissenschaftliche Verlagsgesellschaft mbH, Stuttgart, Gori-Verlag GmbH, Frankfurt, 9th Edition, 1987), corresponding to the classes 4–7, fall under the categories "poorly soluble", "sparingly soluble", "very sparingly soluble" and "virtually insoluble".

The water insolubility of the inventively used α-1,4-D-glucans is expediently such that at least 98%, in particular at least 99.5%, of the polysaccharides used are insoluble in water under standard conditions (T=25° C. +/−20%; p=101325 pascal +/−20%) (conforming to at least classes 4 and 5 according to DAB).

Advantageously the water insolubility of the α-1,4-D-glucans corresponds to classes 6 or 7 according to DAB.

Linear α-1,4-D-glucans are taken to mean α-1,4-D-glucans whose degree of branching is a maximum of 4%, that is to say their main chain has a maximum of four side chains per 100 monosaccharide units.

Expediently, the degree of branching of the water-insoluble linear α-1,4-D-glucans in the 6 position is no more than 0.5%. In the 2 or 3 position the degree of branching is no more than 1% and, in particular, no more than 0.5%.

Particular preference is given to water-insoluble linear α-1,4-D-glucans which have no branches, or whose degree of branching is so minimal that it is no longer detectable using conventional methods.

The weight-average molecular weights $M_w$ (determined by gel permeation chromatography in comparison with a calibration using Pullulan standard) of the inventively used water-insoluble linear α-1,4-D-glucans can vary within a wide range. Expediently, the water-insoluble linear α-1,4-D-glucans used as starting material have a molecular weight $M_w$ of from $0.75 \times 10^2$ to $10^7$ g/mol, preferably from $10^3$ to $10^6$ g/mol, and particularly preferably from $10^3$ to $10^5$ g/mol. A very particularly advantageous range is between $2 \times 10^3$ g/mol and $8 \times 10^3$ g/mol.

Particularly preferably, the water-insoluble linear α-1,4-D-glucans used have a high content of polymers having a degree of polymerization between 10 and 35. Advantageously, at least 25%, preferably at least 30%, and particularly preferably at least 35%, of the α-1,4-D-glucan molecules used have a degree of polymerization of from 10 to 35.

The polydispersity $M_w/M_n$ of the water-insoluble linear α-1,4-D-glucans used can vary within wide ranges. Preferred values of polydispersity are in the range from 1.01 to 50, in particular from 1.5 to 15. The use of glucans having a low polydispersity, however, is preferred because of the better reproducibility of the resultant products.

The α-1,4-D-glucans used can also be chemically modified in a manner known per se, provided that the modifications are harmless with respect to the foodstuffs and medicaments to be produced. Thus, the α-1,4-D-glucans can be chemically modified in a manner known to those skilled in the art by etherification or esterification in the 2, 3 or 6 position. (See also Functional Properties of Food Components, 2nd Edition, Y. Pomeranz, Academic Press (1991); Lehrbuch der Lebensmittelchemie [Textbook of Food Chemistry], Belitz & Grosch, Springer Verlag (1992); Citrate Starch Possible Application as Resistant Starch in Different Food Systems, B. Wepner et al., European Air Concerted Action, Abstract: air3ct94-2203, Functional Properties of Non-digestible Carbohydrates, Pro Fibre Symposium, Lisbon, February 1998, page 59). Preferably, however, chemically unmodified α-1,4-D-glucans are used.

The inventively used water-insoluble linear α-1,4-D-glucans can be of any origin.

For example, the water-insoluble linear α-1,4-D-glucans can be obtained from natural plant and animal sources or from microorganisms which produce such glucans, by conventional isolation and purification.

Since most of the natural sources do not contain the desired water-insoluble linear α-1,4-D-glucans in the desired amounts, however, these polysaccharides are advantageously produced by a biotechnological route. For example, the natural producers of the water-insoluble linear glucans can be genetically modified in such a manner that, compared with the unmodified organism, they have a higher content of unbranched, or only very slightly branched, polysaccharides.

The desired water-insoluble linear α-1,4-D-glucans can also be obtained from highly branched glucans by chemical or enzymatic debranching, for example using debranching enzymes such as pullulanases.

Preferably, the inventively used α-1,4-D-glucans are produced by biotransformation or biocatalytically.

Biotransformation or biocatalytic production is taken to mean here that the water-insoluble α-1,4-D-glucan is produced in vitro by catalytic polymerization of glucose molecules in the presence of a suitable enzyme, in particular an enzyme having amylosucrase activity, under suitable conditions.

An advantageous biocatalytic process for producing water-insoluble linear α-1,4-D-glucans is described in WO 95/31553, whose disclosed content is expressly subject matter of the present description. According to the process of WO 95/31553, the α-1,4-D-glucan is produced by means of a biocatalytic process from sucrose in the presence of an enzyme having amylosucrase activity, in particular amylosucrase from bacteria of the species *Neisseria polysaccharea*. These enzymes catalyze the formation of α-1,4-glycosidically linked glucans by transferring to the growing polymer chain the glucosyl radical of the sucrose molecule, with release of D-fructose, in accordance with the following reaction equation

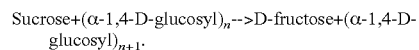

A particularly preferred process for producing water-insoluble linear α-1,4-D-glucans based on the above reaction equation is described in the earlier German patent application DE-A-198 27 978.1, which was not published before the present application, the disclosed content of which is expressly the subject matter of the present description. In this case the water-insoluble linear α-1,4-D-glucans are synthesized from sucrose by means of enzymes having amylosucrase activity, preferably from *Neisseria polysaccharea*, in aqueous buffer-free systems. The reaction can also be carried out in the presence of a water-soluble linear or branched α-1,4-D-glucan, for example a water-soluble dextrin or a water-soluble amylose, since such glucans act as glucosyl group acceptors, on which the enzyme catalyzes an α-1,4-glucan chain extension.

In the course of such a chain extension, water-insoluble linear polysaccharides within the meaning of the present invention are also produced from branched polysaccharides, since the degree of branching of the glucosyl group acceptor decreases greatly with increasing chain extension, i.e. an increasing degree of polymerization. For this purpose the sucrose is used in a high molar excess to the acceptor. In this manner α-1,4-D-glucans can be produced having a molecular weight in the range from $0.75 \times 10^2$ g/mol to $10^7$ g/mol. The linear oligomeric or polymeric acceptors can either be added from the outside, or they can also be generated from sucrose by the amylosucrase itself.

The resistant starch is formed by retrogradation of the nonresistant water-insoluble linear α-1,4-D-glucans.

The α-1,4-D-glucans can be retrograded by processes known per se, for example by heating or by extrusion.

A particularly preferred process for producing resistant starch is described in the earlier DE-A-198 30 618, which was not published prior to the present application, which is expressly incorporated here by reference and whose disclosure is the subject matter of the present description. This process is simple to carry out and yields α-1,4-D-glucan preparations having a high resistant starch content.

In an advantageous embodiment in accordance with the abovementioned DE-A-198 30 618, the resistant starch is produced by first preparing an aqueous suspension or dispersion of the α-1,4-D-glucans. This suspension or dispersion is then heated, for example to a temperature of from 50° C. to 100° C., and then the resultant gel is cooled to a temperature, preferably in the range from 35° C. to freezing point, at which the α-1,4-D-glucan retrogrades, and is then if appropriate dried.

The terms "suspension", "dispersion" and gel in this case have the meaning familiar to those skilled in the art (see also Römpp, Chemie-Lexikon [Chemistry Lexicon], 9th Edition, Thieme-Verlag).

In another embodiment according to DE-A-198 30 618, the resistant starch is produced by freezing the aqueous suspension or dispersion of the α-1,4-D-glucans, the α-1,4-D-glucan being retrograded. After thawing, the product is then if appropriate dried or dewatered.

The complete or partial retrogradation of the water-insoluble linear α-1,4-D-glucans and the formation of resistant starch can be carried out before the α-1,4-D-glucans are combined with the food additives and feed additives. It can take place during combination of the constituents of the composition or it can take place in the mixture of water-insoluble linear α-1,4-D-glucans, additives and if appropriate other constituents.

Food additives and feed additives here are taken to mean not only substances but also microorganisms which are added to foods or feeds to affect or achieve certain properties or activities. These include, in particular, additives which have a positive effect on the health and well-being of humans and animals.

The food additives and feed additives can be probiotics, prebiotics or other additives.

Probiotics are taken to mean nonpathogenic microorganisms which are added to the food or feed alive or in spore form and which can beneficially affect the intestinal flora.

Examples of microorganisms suitable as probiotics are, in particular, bacteria and fungi. Preferred microorganisms are lactic acid bacteria, in particular of the genus *Lactobacillus*, for example Bifidobacteria, microorganisms of the genus *Streptococcus*, for example *Enterococcus* strains, and yeasts, for example of the genus *Saccharomyces*, in particular of the species *Saccharomyces boulardii*.

Prebiotics are taken to mean digestible substances which are added to the foods or feeds and which promote the growth of certain bacteria in the large intestine.

Examples of prebiotics are, in particular, dietary fibers, for example dietary fibers such as oligosaccharides and polysaccharides, for example inulin, oligofructoses, oligofructans and fructooligosaccharides.

Other additives are vitamins and provitamins, in particular vitamin A, the vitamins $B_1$, $B_2$, $B_3$, $B_5$, $B_6$, $B_9$ and $B_{12}$, vitamin C, vitamin D, vitamin E, vitamin F and vitamin K; antioxidants; oils, fats and fatty acids, in particular polyunsaturated fatty acids, for example Ω-3-fatty acids or essential fatty acids such as linoleic acid and linolenic acid; also herbs and extracts.

Preferably, combinations of α-1,4-D-glucans and/or resistant starch and food additives and feed additives can be used which, firstly, do not change the technical preconditions for processing of food and, secondly, do not significantly affect the property profile of the food. This is the case, for example, if the caloric content of the food is not changed by the functional additives. This is achieved either by both or a plurality of functional additives being neutral with respect to specific properties, or the positive or negative effect of a functional constituent being precisely abolished by the negative or positive effect of the other functional constituent.

Compositions are particularly advantageous which, in addition to the water-insoluble linear α-1,4-D-glucan and/or the resistant starch, which is itself a prebiotic, comprise probiotics. Preferably, the probiotic is a Bifidobacterium. This combination leads to an unexpected symbiotic effect, in that the resistant starch is digested by the intestinal microorganisms with the formation of short-chain fatty acids which in turn serve as nutrient for the Bifidobacteria and promote their proliferation.

The inventive compositions can be produced by simple mixing.

In a particularly advantageous embodiment, the water-insoluble linear α-1,4-D-glucan or the resistant starch obtainable therefrom serves as carrier for at least one food additive or feed additive.

In a further preferred embodiment, the water-insoluble linear α-1,4-D-glucan or the resistant starch obtainable therefrom occurs in the form of microparticles, in particular spherical microparticles, which consist in whole or in part of the glucan. This is particularly advantageous if the water-insoluble linear α-1,4-D-glucan or the resistant starch obtainable therefrom is to serve as carrier for the food additive or feed additive.

Spherical microparticles in this case are taken to mean approximately spherical microparticles whose deviation in axial lengths from the ideal state of a sphere which is described by axes of the same length which depart from a common origin, are directed into space and define the radius of the sphere in all spatial directions, is no more than 40%. Preferably, spherical microparticles are used which have deviations of no more than 25%, particularly preferably no more than 15%.

The specific surface area of the microparticles is expediently in a range from 1 m$^2$/g to 100 m$^2$/g, preferably from 1.5 m$^2$/g to 20 m$^2$/g, and particularly preferably from 3 m$^2$/g to 10 m$^2$/g.

The mean diameter (number average) of the microparticles is expediently in a range from 1 nm to 100 μm, preferably from 100 nm to 10 μm, and particularly preferably from 1 μm to 5 μm.

The dispersity $D = d_w/d_n$ of the microparticles, where $d_w$ is the weight average of the diameter and $d_n$ is the number average of the diameter of the microparticles, is expediently in a range from 1 to 10, preferably from 1.5 to 5, and preferentially from 2 to 3. The means $d_w$ and $d_n$ are defined as $$d_n = \Sigma n_i \times d_i / \Sigma n_i; \text{ and}$$

$$d_w = \Sigma n_i \times d_i^2 / \Sigma n_i \times d_i$$

where $d_i$ is the diameter of the particles of species i;

$n_i$ is the number of particles i having the diameter di; and i is a serial parameter.

The term weight in this context does not mean mass, but a weighted mean, as a result of which the larger diameters have a higher value. The exponent 2 gives diameters of larger particles more weight.

Microparticles which consist in whole or in part of resistant starch can be formed by simple grinding of the resistant starch which was obtained from the above-described gel.

Further processes for producing microparticles are described in the earlier German patent applications DE-A-197 37 481.6, DE-A-198 39 214.1, DE-A-198 39 216.9 and DE-A-198 39 212.5, which are hereby expressly incorporated by reference and whose disclosure is also a component of the present description.

The preferably spherical microparticles are expediently prepared by dissolving the water-insoluble α-1,4-D-glucans or the resistant starch obtainable therefrom in a solvent which is safe for foods, for example by dissolution in aqueous alkali, introducing the solution into a precipitant, preferably water, cooling the resultant mixture to, preferably, from 10° C. to −10° C. and separating off the microparticles formed.

Structure and surface of the microparticles can be controlled by the type of precipitant. By the concomitant use of suitable additives, in particular those permitted for use in foods, for example sugars such as fructose, sucrose and glucose, the structure, size and surface of the particles can also be affected.

The concentration of the α-1,4-D-glucan or the resistant starch in the solution can vary within a broad range and is preferably from about 0.1 to 1 g per ml of solvent.

Microparticles having a mean size from 0.1 μm to 3 μm may advantageously be obtained by this process if a hot-water-soluble α-D-glucan is added to the precipitant.

The porosity of the microparticles may also be controlled by choosing the process for producing the water-insoluble linear α-1,4-D-glucan. Thus, for example, by adding aids in the biotechnological production of the polysaccharides, the porosity of the microparticles obtained from such polysaccharides may be affected. In particular, it has been found that the porosity of microparticles which are formed in whole or in part from the water-insoluble linear α-1,4-D-glucans can be increased if the glucan is produced from sucrose by means of amylosucrase in the presence of a glucosyl group acceptor, for example dextrin. In this case the microparticles are all the more porous, the higher the concentration of the glucosyl group acceptor during the biotransformation.

The food additives and feed additives can be applied to the carrier material, for example, in the case of liquid food additives and feed additives such as unsaturated fatty acids, by simple mixing. The additives, however, can also be added to the precipitation bath from which the microparticles are obtained. During the formation of the microparticles the additives then adsorb on the surface of the particles.

In a further advantageous embodiment, the food additives and feed additives are at least partially enrobed or encapsulated by the water-insoluble linear α-1,4-D-glucans or the resistant starch. In this manner, not only is the synergistic or symbiotic action amplified, but also an additional stabilizing effect is achieved. This embodiment is particularly advantageous in the case of a combination of water-insoluble linear α-1,4-D-glucans and/or resistant starch with probiotics, the living organisms being encapsulated by a layer of resistant starch and, if appropriate, other polysaccharides, and by this means also being protected against harmful effects which occur, for example, during the processing of foodstuffs.

The enrobing can be performed in a manner known per se by aqueous dispersion processes or suspension processes.

The compositions can consist solely of the water-insoluble linear α-1,4-D-glucans and/or the resistant starches obtainable therefrom and the respective additives, or can contain other additives, for example other food supplements.

The inventive compositions can comprise the water-insoluble linear α-1,4-D-glucans in non-α-amylase-resistant form, in the form of the resistant starch obtainable therefrom, or in the form of mixtures thereof.

In a possible embodiment, the inventive composition comprises the glucans predominantly as water-insoluble linear α-1,4-D-glucans, that is to say in non-α-amylase-resistant form. Such compositions are suitable, for example, for producing foods and food precursors where the resistant starch is formed only by a further treatment or processing prior to consumption, for example by heating.

In a further embodiment, the inventive composition comprises the glucans predominantly in the form of resistant starch. Such compositions can be added to the foodstuffs, for example even after processing steps such as warming or heating. In such compositions, the resistant starch content, based on the total amount of α-1,4-D-glucan, is chosen to be as high as possible. Expediently, the content, as determined by Englyst (see above), is at least 25% by weight, preferably at least 65% by weight, in particular 75% by weight, and particularly preferably at least 90% by weight, in particular from 95 to 99% by weight or more.

The inventive compositions can be used in a multiplicity of foodstuffs. Examples of suitable foods are milk and milk products such as yoghurt, quark or slices and milk pudding; bread, spreads, drinks, muesli bars, cereals, cookies, cakes, bakery products, sauces, noodles, mashed potato and other potato dishes such as french fries, soufflés, thickeners, designer drinks, drinks powders and ready-to-eat dishes.

Resistant starch based on water-insoluble linear α-1,4-D-glucans and their compositions can be used as a substitute for foodstuff constituents, in particular as a fat substitute, and thus serve as a calorie reducing agent. In this manner they can effect a cell stimulation and stimulate the appetite.

Degradation of the resistant starch in the intestine to form short-chain fatty acids, in particular to form particularly advantageous butyrate, its suitability as a substitute and the synergistic and symbiotic effects in combination with other food additives or feed additives, however, are not the sole advantage in the use of resistant starch in foodstuffs. This is because resistant starch can, in particular together with other food additives or feed additives, also be used for improving the properties of the foods. Thus, the inventive composition, depending on the choice of the additives, can lead to an increase in gel formation, an improvement in flow properties, an increase or decrease in viscosity, an improvement in sorption behavior, an increase or decrease in swelling properties and an improvement in the gelatinization temperature of products which comprise polysaccharides. The inventive composition can likewise be used to affect the solubility, transparency and texture of the gel structure, and to improve the heat stability, cold stability, acid stability and shear stability of the products. In addition, use of the inventive compositions can increase the film-formation tendency, beneficially affect the freezing and thawing stabilities and improve digestibility. In addition, coating effects can also come into play, which are based on the taste, mouth feel or odor.

The fact that the resistant starch obtainable from water-insoluble linear α-1,4-D-glucans supplies during digestion a somewhat high content of butyrates which are favorable for the intestinal flora also makes this starch suitable for use in medical and veterinary preparations, in particular in combination with other functional additives, for example the abovementioned food additives and feed additives, also together with other therapeutic agents. The use of resistant starch based on water-insoluble linear α-1,4-D-glucans as medicament, alone or in combination with other functional additives, has a beneficial effect on the numerous causes of disease. Thus, medicaments based on the inventive resistant starch are suitable, for example, for treating heart disorders, gastrointestinal disorders, arthritis, immunological disorders, mental dysfunctions, nerve disorders, psychic disturbances, sleep disturbances, disorders of the musculature, diseases which affect the hormone balance, thyroid disorders, diseases of the internal organs, changes in blood spectrum, circulatory disorders, allergies, skin disorders and disorders due to malnutrition. Also, preparations containing resistant starch can be used as appetite stimulators.

Accordingly, resistant starch based on water-insoluble α-1,4-D-glucans, alone or in combination with other functional additives, can also be used as medicament, more precisely both as therapeutic agents and as prophylactics or diagnostics. The medical preparations comprising resistant starch can comprise in this case customary aids and carriers and can be present in the customary administration forms, for example in the form of tablets, slow-release formulations or agents having controlled release of active compound.

The present invention is described in more detail by the examples below:

EXAMPLES

Example 1

Production of α-1,4-D-glucans 5 l of a sterilized 30% strength sucrose solution were placed in a 5 l vessel. An enzyme extract which contained amylosucrase from *Neisseria polysaccharea* (WO-A-95/31553) was added in one portion and the solution was mixed. The enzyme activity used was 148 000 units in this experiment. The closed vessel was incubated at 37° C. During the biotransformation period, a white precipitate formed. The reaction was terminated after 39 h. The precipitate was centrifuged off, frozen at −70° C. and then freeze-dried. The mass of the freeze-dried solid was 526.7 g (70.2% yield).

To separate off low-molecular weight sugars, 200 g of the solid were washed with water for 30 min, with stirring at room temperature, frozen at −70° C. and freeze-dried. The fructose and sucrose contents were, after dissolving the solid in DMSO, determined by a coupled enzymatic assay and the fructose content was 4.61 mg of fructose per 100 mg of solid (4.6%); the sucrose content was below the limit of detection.

The supernatant of the biotransformation was denatured at 95° C. After cooling to room temperature it was again centrifuged. The clear supernatant was frozen at −70° C. and thawed at 4° C. over 3 days. The precipitate thus produced was frozen at −70° C. and freeze-dried.

To separate off low-molecular weight sugars, 39.5 g of the solid were washed with water for 30 min, with stirring at room temperature, frozen at −70° C. and freeze-dried. The fructose and sucrose contents were, after dissolving the solid in DMSO, determined by a coupled enzymatic assay as described by STITT et al. (Meth. Enzym., 174 (1989) 518–552) and the fructose was 2.27 mg of fructose per 100 mg of solid; the sucrose content was below the limit of detection.

Example 2

Determination of the molecular weight of the material obtained as described in Example 1

2 mg of the α-1,4-D-glucan from example 1 were dissolved at room temperature in dimethyl sulfoxide (DMSO, analytical grade from Riedel-de-Haen) and filtered. A portion of the solution was injected into a column for gel-permeation chromatography. The elution medium used was DMSO. The signal intensity was measured by an RI detector and assessed against a pullulan standard (Polymer Standard Systems). The flow rate is 1.0 ml per minute.

The measurement gives a number-average molecular weight (Mn) of 2 326 g/mol and a weight-average molecular weight (Mw) of 3 367 g/mol. The recovery rate is 100%.

Example 3

Determination of the RS Content 200 mg (dry weight) of the pulverulent product to be analyzed for its RS content were incubated with the described enzyme mixture at pH 5.2 for 120 min according to the method of Englyst et al. (Eur. J. Clin. Nutrition, 46 (1992) (Suppl. 2) pp. 33–550) to determine the RS content. After terminating the enzymatic degradation, the activity of the enzymes was stopped by reducing the pH to a value of 3 and the temperature to 20° C. The solution was then made 80% strength (v/v) ethanol by adding 4 times the amount of ethanol. The 80% strength ethanolic solution was allowed to stand for 1 h at room temperature. The precipitate was centrifuged (2 500×g, 10 min) and the supernatant was discarded. The residue was washed three times with 80% strength (v/v) ethanol and once with absolute ethanol and centrifuged. The residue was lyophilized and weighed. The dry matter of the residue was determined and the RS content was calculated from the equation below:

$RS[\%] = 100 \times \text{weight of the residue (dry weight)/initial weight (dry weight)}$

Examples 4 to 7

A linear, nature-identical α-1,4-D-glucan from example 1 was heated in aqueous solution and a gel formed. This gel was made 10% by weight in solids content and portioned. The portions were retrograded at 4 and 25° C. (examples 5 and 6) or using a stepped program (example 7). In addition, the linear carbohydrate polymer from the reaction solution was frozen out (example 4). The retrograded samples were dried and the RS content was determined as described above.

Table 1 illustrates the effect of the retrogradation temperature and retrogradation conditions on the RS content in the product produced from a 10% gel of the α-1,4-D-glucans used by retrogradation for 24 hours.

TABLE 1

| Example | Retrogradation temperature | RS (% by weight) |
|---|---|---|
| 4 | −70° C. | 78 ± 4 |
| 5 | 4° C. | 70 ± 2 |
| 6 | 25° C. | 87 ± 1 |
| 7 | stepped program | 74 ± 3 |

The example in table 1 shows that the retrogradation temperature affects the RS content. Thus retrogradation at 25° C. leads to a significantly higher RS content compared with retrogradation at 4° C. In contrast, retrogradation at −70° C. gives a slightly higher RS content compared with that after retrogradation at 4° C.

Example 8

Determination of the solubility of α-1,4-D-glucans and classification in accordance with the German Pharmacopeia (DAB)

564 mg of α-1,4-D-glucan from example 1 were heated in approximately 0.5 l of twice-distilled water at 1.3 bar and 130° C. for 1.5 hours in an autoclave (Certoclav apparatus). The weight of the reaction vessel was measured in advance. The apparatus is then depressurized and cooled at room temperature. The contents are weighed. They correspond to 501.74 g. After a further 24 hours, the contents are centrifuged and decanted. The solid residue is dried and weighed. This is 468 mg. This gives a dissolved portion of 96 mg. Based on the solvent used, it is calculated that 5 226 mg of water are required for 1 mg of α-1,4-D-glucan. According to the classification of the DAB, this gives the grading that this substance is "very sparingly soluble", since between 1 000 and 10 000 parts of solvent are necessary to bring 1 part of the substance into solution. This corresponds to solubility class 6, according to the DAB.

Example 9

Determination of the solubility of α-1,4-D-glucans and classification according to the German Pharmacopeia (DAB)

The experiment was carried out in accordance with example 8 using α-1,4-D-glucan obtained in a similar manner as in example 1. The sole difference was a cooling process which was carried out downstream of the autoclave treatment and the cooling to room temperature. The mixture of substances is kept for 3 hours at 5° C.

526 mg of α-1,4-D-glucan were weighed onto approximately 480 ml of twice-distilled water. After the thermal treatment, the weight was 468.09 g. The dried sediment was 488 mg. Accordingly, 38 mg of the α-1,4-D-glucan had passed into solution. This corresponded to a ratio of 1 mg of substance to 12 305 parts of solvent. Therefore, the substance was to be classified by this treatment method into class number 7 according to DAB and therefore to be classified as virtually insoluble, because more than 10 000 parts of solvent were required for 1 part of substance.

Example 10

Production of Muesli Bars Containing Resistant Starch

Muesli bars were produced with varying amounts of resistant starch (RS).

| Base formula: | 40% honey |
| | 30% oatflakes |
| | 6% sunflower seeds |
| | 9% hazelnuts |
| | 6% oatflakes |
| | 9% chocolate flakes |
| a) | 40% honey |
| | 30% oatflakes |
| | 6% sunflower seeds |
| | 9% hazelnuts |
| | 6% oatflakes |
| | 9% chocolate flakes |
| | 3% amylose (RS) |
| b) | 40% honey |
| | 24% oatflakes |
| | 6% sunflower seeds |
| | 9% hazelnuts |
| | 6% oatflakes |
| | 6% chocolate flakes |
| | 9% amylose (RS) |
| c) | 36% honey |
| | 24% oatflakes |
| | 6% sunflower seeds |
| | 9% hazelnuts |
| | 6% oatflakes |
| | 6% chocolate flakes |
| | 9% amylose (RS) |
| | 4% highly unsaturated fatty acids |
| d) | 40% honey |
| | 21% oatflakes |
| | 6% sunflower seeds |
| | 9% hazelnuts |
| | 6% oatflakes |
| | 6% chocolate flakes |
| | 12% amylose (RS) |

The ingredients were mixed well and baked in a drying cabinet or oven for approximately 4 hours at 70° C. The muesli bars, even with a content of resistant starch, could not be differentiated in their consistency from the bars made according to the base formula and tasted good.

Example 11

Study of the formation of short-chain fatty acids (SCFA) by in vitro fermentation of the α-amylase-resistant components by freshly taken feces samples.

1 ml of a 5% strength feces suspension (15 g of freshly taken human feces in 50 ml of Soerensen buffer, pH 6.5; buffer of potassium hydrogenphosphate and disodium hydrogenphosphate dihydrate) was mixed in nitrogen gas-treated cryo tubes each with 10 mg of resistant structures corresponding to example 1 which were isolated by enzymatic hydrolysis and, as a comparison, of Novelose, retrograded cornstarch, National Starch & Chemical, USA, and homogenized. Fermentation was effected at 37° C. Samples were taken every hour and frozen.

The concentration of short-chain fatty acids was determined in a fecal suspension using gas chromatography on a capillary column (Carbowax 20M) using a temperature program. The GC system used was an HP 5890 series II station with an HP 7673 GC/SCF injector, HP GC autosampler controller, detector FID; software—HP Chemstation. Helium was used as mobile phase.

200 mg of the fecal suspension were suspended with four times the amount of water and homogenized. Of this diluted working fecal suspension, a portion was used for the dry matter determination.

500 mg of the working fecal suspension were centrifuged. 100 μl of the supernatant were admixed with 25 μl of 1 M sodium hydroxide solution. The sealed vessel was placed with a bored cover into liquid nitrogen and freeze-dried. The dried sample was admixed with 100 μl of 5M formic acid and 400 μl of acetone and shaken on a vortex mixer. The organic phase which formed was decanted into autosample vials which were immediately closed. From these 1 μl was injected each time into a GC. The external standards used were acetic acid, propionic acid, butyric acid, isobutyric acid, valeric acid and isovaleric acid (Supelco).

The resistant structures were fermented in parallel in duplicate fermentation studies.

The fermentability of the structures used was found to vary. In particular, the formation rates and the spectra of the short-chain fatty acids varied.

In vitro fermentation of the resistant structures corresponding to example 1 achieved significantly higher levels of short-chain fatty acids and butyrate in comparable fermentation times. Whereas 8-hour fermentation of the resistant structures according to example 1 established an SCFA level of approximately 2 000 μmol/g of dry matter, the butyrate content being about 60%, the SCFA level after the same fermentation time of resistant structures from Novelose was only approximately 750 μmol of dry matter. The butyrate in this case was present with a content of approximately 35%. Fermenting resistant structures of the water-soluble α-1,4-D-glucan used according to the invention as starting product therefore produces butyrate more rapidly and in greater quantity than the resistant starch of Novelose.

bifido bacteria by the overall sum and multiplying by 100. The relative change in the overall sum of the bifido bacteria was calculated by multiplying the number of bifidos per gram of feces by the weight of the feces. This number at the start of the study was set equal to 100. The comparison value after 14 days was related to this standard value of each individual subject. The values of the study are summarized in table 2. The relative contents of the bifido bacteria are reported as mean values over time and the subjects. The relative contents of bifido bacteria in the total number of microorganisms is reported as a value relative to the base 100, the value before treatment with $LC_1$ or RS bifido, on the basis of the 14-day final value. The results show that there was an increase in the daily amount of feces, more precisely a higher increase when RS bifido was used. The pHs decreased by approximately 0.5. Furthermore, the beneficial effect on the intestinal epithelial cells can be seen from the sharp rise in short-chain fatty acids. This effect is not observed with the bifido bacteria alone.

TABLE 2

|  | before $LC_1$ | after $LC_1$ | before RS bifido | after RS bifido |
| --- | --- | --- | --- | --- |
| Feces weight (g/day) | 125 +/− 29 | 137 +/− 35 | 127 +/− 32 | 148 +/− 35 |
| Relative change in fecal mass | 100 | 110 | 100 | 116 |
| Feces pH | 6.6 +/− 0.5 | 5.9 +/− 0.5 | 6.5 +/− 0.5 | 6.0 +/− 0.5 |
| Total number of microorganisms per g of feces | $8.5 \times 10^8$ +/− $0.2^8$ | $9.2 \times 10^8$ +/− $0.2^8$ | $8.6 \times 10^8$ +/− $0.2^8$ | $11.2 \times 10^8$ +/− $0.2^8$ |
| Relative content of the bifido bacteria (%) | 9.9 +/− 0.2 | 10.3 +/− 0.2 | 9.9 +/− 0.2 | 13.9 +/− 0.2 |
| Relative content of bifido bacteria in the total number of microorganisms | 100 | 195 | 100 | 255 |
| Acetate μmol/g dry matter of feces* | 365 +/− 15 | 335 +/− 15 | 387 +/− 15 | 1021 +/− 15 |
| Propionate μmol/g dry matter of feces* | 87 +/− 15 | 91 +/− 15 | 89 +/− 15 | 675 +/− 15 |
| Butyrate μmol/g dry matter of feces* | 99 +/− 15 | 100 +/− 15 | 102 +/− 15 | 617 +/− 15 |

*after 6 hours of fermentation (= saturation value)

Example 12

Effect of a combination of resistant starch and bifido bacteria on the activity and growth of bifido bacteria and intestinal cells To test the effect of the combination of resistant starch and bifido bacteria on intestinal flora, 10 g of resistant starch, produced as described in examples 4 to 7, were administered to 5 healthy subjects for oral intake over a period of 14 days. The samples were consumed during breakfast in the form of a bifido bacteria-containing yoghurt into which the polyglucan was stirred (yoghurt LC, from Nestle). The subjects had a mean age of 38.9 and a mean weight of 67.3 kg. The test values were compared with a control. The control group consisted of the same subjects. They were studied 3 months before the second study. Yoghurt containing bifido bacteria without RS was consumed. For 10 weeks before the start of the control study and in the roughly 10 weeks before termination of the first control study until the second study (RS bifido), the subjects consumed no yoghurt or similar foods which contain bifido bacteria. The absolute amount of bifido bacteria was determined in accordance with a method first published in the following references ("A Color Atlas of Anaerobic Bacteria", 1984, pages 53–65, T. Mitsuoka (Editor), published by Kabushiki Kaisha Sobunsha, Tokyo, Japan (1984)). The colonies that grew were cultured in different media, evaluated for the genotype and enumerated. The overall sum of all microorganisms was seen to be the overall sum of the microorganisms of each individual subject. The relative number of the bifido bacteria was determined by dividing the number in the enumeration of the Exampl 13

Production of here, for example, polyglucan-deposited cookies having a reduced calorie content a) Comparison Example 20 g of sugar and 50 g of soft butter are whipped to a foam. Then half an egg, 50 g of wheat flour, 30 g of ground hazelnuts, 1 teaspoon, a little lemon peel, 1 teaspoon of baking powder and 1 teaspoon of vanilla sugar are added. The mixture is stirred well until it is very dry and crumbly. A little milk is added and stirred so that the batter may readily be picked up. 1 teaspoon of the mixture is placed each time on a baking sheet. In the preheated baking oven (hot air), the cookies are baked for about 15 minutes at 175° C.

Production of baked goods containing wheat flour (comparison example) and polyglucan-deposited cookies b)

The procedure is carried out as in example 13a, but instead of the sugar (sucrose), approximately 20 g of polyglucan are used (including 1 teaspoon of vanilla sugar). In order to achieve an acceptable sweetness, the sweetening was carried out using a commercial sweetener (for example Natreen) in an equivalent dose.

Test subjects (8) verified that in the criteria associated with taste, such as mouth feel, crispness effect, consistency, stickiness, bite effects and chewing effects and chewing feel and sweetness, no noticeable difference could be perceived, or if a difference was found, that this was not considered disadvantageous. The baked goods in the form of cookies taste good. Thus there is a possible use as bulking agent, as sugar substitute, especially in foods, but also beverages, for example milk drinks, drinking yoghurts.

The invention claimed is:

1. A functional food or functional feed composition comprising a resistant starch obtained by retrogradation of a water-insoluble linear α-1,4-D-glucan including heating to 50° C.–100° C. and retrograding at 35° C. to freezing point, said polyglucan being produced by the action of amylosucrase acting on sucrose, the composition further comprising at least one further food additive or feed additive.

2. The composition as claimed in claim 1, wherein the food additive or feed additive is selected from the group consisting of probiotics, prebiotics, vitamins, provitamins, antioxidants, oils, fats, fatty acids, and mixtures thereof.

3. The composition as claimed in claim 2, wherein the probiotic is a bifido bacterium.

4. The composition as claimed in claim 1, wherein the resistant starch acts as a carrier material for the food additive or feed additive.

5. The composition as claimed in claim 1, wherein the resistant starch is present in the form of microparticles with a mean diameter of 1 nm to 100 μm.

6. The composition as claimed in claim 1, wherein the food additive or feed additive is at least in part enrobed by the resistant starch.

7. The composition as claimed in claim 1, wherein the water-insoluble linear α-1,4-D-glucan has a molecular weight of from $0.75 \times 10^2$ to $10^7$ g/mol.

8. The composition as claimed in claim 1, wherein the water-insoluble linear α-1,4-D-glucan has a molecular weight of from $10^3$ to $10^6$ g/mol.

9. The composition as claimed in claim 1, wherein the water-insoluble linear α-1,4-D-glucan has a molecular weight of from $10^3$ to $10^5$ g/mol.

10. The composition as claimed in claim 1, wherein the water insoluble linear α-1,4-D-glucan is obtained by in vitro polymerization of glucose in the presence of an enzyme having amylosucrase activity.

11. The composition as claimed in claim 1, wherein the composition is a foodstuff, a foodstuff precursor or a foodstuff supplement.

12. A medicament comprising a resistant starch obtained by retrogradation of a water-insoluble linear α-1,4-D-glucans including heating to 50° C.–100° C. and retrograding at 35° C. to freezing point, said polyglucan being produced by the action of amylosucrase acting on sucrose, and wherein the resistant starch contains no phosphorous.

13. The medicament as claimed in claim 12, wherein the medicament is a gastrointestinal composition.

14. A pharmaceutical or veterinary composition comprising a resistant starch obtained by retrogradation of a water-insoluble linear α-1,4-D-glucans including heating to 50° C.–100° C. and retrograding at 35° C. to freezing point, said polyglucan being produced by the action of amylosucrase acting on sucrose, and wherein the resistant starch contains no phosphorous.

15. The composition as claimed in claim 14, further comprising a functional additive.

16. The composition as claimed in claim 15, wherein the functional additive is a food additive or feed additive.

17. The composition as claimed in claim 16, wherein the food additive or feed additive is a probiotic.

18. The composition as claimed in claim 17, wherein the probiotic is a bifido bacterium.

19. The composition as claimed in claim 15, wherein the functional additive is a medicinal compound.

20. The composition as claimed in claim 19, wherein the medicinal compound is a therapeutic agent.

21. A method of treating or preventing gastrointestinal disorders comprising administering an effective amount of a medicament comprising a resistant starch obtained by retrogradation of a water-insoluble linear α-1,4-D-glucans including heating to 50° C.–100° C. and retrograding at 35° C. to freezing point, said polyglucane being produced by the action of amylosucrase acting on sucrose, and wherein the resistant starch contains no phosphorous.

* * * * *